United States Patent
Ramesh et al.

(10) Patent No.: US 12,178,389 B2
(45) Date of Patent: Dec. 31, 2024

(54) SYSTEMS AND METHODS FOR ENDOSCOPE TYPE DETECTION

(71) Applicant: Stryker Corporation, Kalamazoo, MI (US)

(72) Inventors: Ajay Ramesh, Pleasanton, CA (US); Chien Mien Pang, San Jose, CA (US)

(73) Assignee: Stryker Corporation, Kalamazoo, MI (US)

( * ) Notice: Subject to any disclaimer, the term of this patent is extended or adjusted under 35 U.S.C. 154(b) by 335 days.

(21) Appl. No.: 17/192,777

(22) Filed: Mar. 4, 2021

(65) Prior Publication Data

US 2021/0275000 A1  Sep. 9, 2021

Related U.S. Application Data

(60) Provisional application No. 62/985,801, filed on Mar. 5, 2020.

(51) Int. Cl.
 *A61B 1/00* (2006.01)
 *A61B 1/06* (2006.01)

(52) U.S. Cl.
 CPC .... *A61B 1/00059* (2013.01); *A61B 1/000095* (2022.02); *A61B 1/00045* (2013.01); *A61B 1/0655* (2022.02); *A61B 1/0661* (2013.01)

(58) Field of Classification Search
 CPC .......... A61B 1/00059; A61B 1/000095; A61B 1/00045; A61B 1/0661
 See application file for complete search history.

(56) References Cited

U.S. PATENT DOCUMENTS

| | | | |
|---|---|---|---|
| 4,951,135 A * | 8/1990 | Sasagawa | A61B 1/05 348/69 |
| 6,204,967 B1 * | 3/2001 | Morishima | H04N 13/31 359/464 |
| 6,436,032 B1 | 8/2002 | Eto et al. | |
| 7,289,139 B2 | 10/2007 | Amling | |
| 8,194,122 B2 | 6/2012 | Amling | |
| 8,373,748 B2 | 2/2013 | Pang et al. | |
| 8,537,210 B2 | 9/2013 | Shimada et al. | |
| 8,882,657 B2 | 11/2014 | Ohline et al. | |
| 9,603,512 B2 | 3/2017 | Hoeg et al. | |
| 10,623,651 B2 * | 4/2020 | Murakita | H04N 7/183 |
| 2002/0156349 A1 * | 10/2002 | Yamaki | A61B 1/0638 600/178 |
| 2003/0076411 A1 * | 4/2003 | Iida | H04N 7/183 348/E7.087 |
| 2004/0092792 A1 * | 5/2004 | Kobayashi | A61B 1/05 600/101 |

(Continued)

FOREIGN PATENT DOCUMENTS

CN  111317426 A * 6/2020

*Primary Examiner* — Anh Tuan T Nguyen
*Assistant Examiner* — Shankar Raj Ghimire
(74) *Attorney, Agent, or Firm* — Morrison & Foerster LLP (57) ABSTRACT

Systems and methods for detecting, characterizing, and addressing the type of endoscope that is connected to the camera/light source based on the image size taken using that endoscope are disclosed. Once the type of endoscope is determined, the systems and methods can adjust at least one parameter of the camera/light source based on the determination of the type of endoscope that is being used.

17 Claims, 5 Drawing Sheets

(56) References Cited

U.S. PATENT DOCUMENTS

| | | | | |
|---|---|---|---|---|
| 2005/0020879 A1* | 1/2005 | Suzuki | H04N 23/663 | |
| | | | 600/109 | |
| 2005/0157168 A1* | 7/2005 | Kaneko | A61B 1/000095 | |
| | | | 348/72 | |
| 2008/0143827 A1* | 6/2008 | Yoshizumi | A61B 1/045 | |
| | | | 348/E7.085 | |
| 2009/0066787 A1* | 3/2009 | Yamazaki | A61B 1/063 | |
| | | | 348/70 | |
| 2010/0048993 A1* | 2/2010 | Shidara | A61B 1/04 | |
| | | | 600/109 | |
| 2012/0127292 A1* | 5/2012 | Yamazaki | A61B 1/0638 | |
| | | | 348/E7.085 | |
| 2012/0127293 A1* | 5/2012 | Yamazaki | H04N 25/136 | |
| | | | 348/71 | |
| 2015/0243027 A1* | 8/2015 | Ichiki | G06V 10/44 | |
| | | | 382/128 | |
| 2016/0234427 A1* | 8/2016 | Yoshino | A61B 1/00036 | |
| 2017/0000314 A1* | 1/2017 | Honda | A61B 1/00052 | |
| 2017/0007095 A1* | 1/2017 | Kutsuma | A61B 1/00059 | |
| 2017/0034437 A1* | 2/2017 | Kutsuma | G06T 5/00 | |
| 2017/0100018 A1* | 4/2017 | Saito | A61B 1/000094 | |
| 2017/0230624 A1* | 8/2017 | Hanawa | H04N 23/12 | |
| 2017/0273541 A1* | 9/2017 | Watanabe | A61B 1/0638 | |
| 2018/0027165 A1* | 1/2018 | Murakita | A61B 1/045 | |
| | | | 348/68 | |
| 2018/0296077 A1* | 10/2018 | Suzuki | H04N 23/63 | |
| 2019/0053693 A1* | 2/2019 | Koiso | A61B 1/00059 | |
| 2019/0069769 A1* | 3/2019 | Kubo | A61B 1/045 | |
| 2023/0115488 A1* | 4/2023 | Shelton | A61B 5/1076 | |
| | | | 600/108 | |

\* cited by examiner

SYSTEMS AND METHODS FOR ENDOSCOPE TYPE DETECTION

CROSS-REFERENCE TO RELATED APPLICATIONS

This application claims benefit of U.S. Provisional Application No. 62/985,801, filed Mar. 5, 2020, the contents of which is incorporated herein by reference in its entirety.

FIELD

The present disclosure relates generally to surgical procedures, and more specifically systems and methods for automatically detecting the type of endoscope employed during a surgical procedure.

BACKGROUND

During a typical endoscopic procedure, one end of the endoscope can be inserted into the body of a patient for viewing internal features of the patient's body while the other end can be connected to a camera/light source. The camera can generate image data based on light received through the endoscope. This image data can be used to display real-time images of the internal features of the patient's body on a display device.

There are various types of endoscopes that can be used for medical procedures. These endoscopes come in various shapes and sizes with different physical and functional characteristics (e.g., diameter, length, type of optics, magnification, materials, degree of flexibility, etc.). For example, flexible endoscopes are typically used in gastroenterology, semi-rigid endoscopes are typically used in urology, and rigid endoscopes are typically used in laparoscopy and arthroscopy.

Because different types of endoscopic procedures can be performed under different conditions, the camera settings can be different depending upon the type of procedure as well as the type of endoscope being used. For example, more light is generally used during laparoscopic procedures; whereas, too much light can be problematic (e.g., produce reflection) during arthroscopic procedures. Besides light source setting, additional parameters such as video gain levels, sharpness levels, camera shutter speed, gamma levels, and others can vary depending on the procedure being performed and endoscope type.

SUMMARY

According to various aspects, systems and methods can detect the type of endoscope that is connected to a camera/light source system. Since there are various types of endoscopes for various types of medical procedures, it can be inconvenient and time-consuming for medical personnel to determine and manually adjust the camera settings based on the specific endoscope and/or procedure to be performed. Applicants have discovered a system and method that can detect the type of endoscope that is connected to the camera/light source system based on the image size taken using that endoscope. Once the type of endoscope is determined, at least one parameter of the camera/light source system can be adjusted dependent on the type of endoscope being used.

In some aspects, use of the systems, methods, and techniques described herein during surgical procedures (e.g., endoscopic, other minimally invasive, or non-invasive surgical procedures) may allow surgeons to have an optimal visual endoscopic video and to focus on the surgical procedure without the distraction of manually assessing, characterizing, adjusting, or addressing the type of endoscope being employed. Furthermore, the systems described herein can also optimize the time of medical personnel by allowing them to avoid having to determine and manually set the camera settings that are appropriate for the type of endoscope being used.

According to various aspects, an endoscopic system comprises one or more processors configured to: receive image data representing an image from a video camera coupled to an endoscope; segment the image into at least two sections; segment each of the at least two sections into a plurality of subsections; calculate a representative pixel value for each of the subsections; determine what type of endoscope is coupled to the video camera based on the representative pixels values for each of the subsections; and adjust a parameter of the video camera based on the type of endoscope.

Optionally, the parameter comprises at least one of video gain level, sharpness level, camera shutter speed, or gamma level.

Optionally, the video camera comprises a light source. In some embodiments, the parameter comprises light source setting.

Optionally, the parameter is a parameter for processing or displaying images acquired by the video camera.

Optionally, the type of endoscope determined is dependent upon a physical characteristic of the endoscope.

Optionally, the physical characteristic of the endoscope comprises a size of a scope mask of the endoscope.

Optionally, calculating the representative pixel value for each of the subsections comprises calculating a representative luminance for a plurality of pixels within each subsection.

Optionally, determining what type of endoscope is coupled to the video camera comprises comparing the representative luminance for each subsection with threshold luminance values for each subsection for a given endoscope type.

Optionally, a boundary of each section is defined by a vertical line through a center of the image, a horizontal line through the center of the image, and/or an image boundary line.

Optionally, the image is segmented into four sections.

Optionally, a boundary of each section is defined by a vertical line through a center of the image, a horizontal line through the center of the image, and an image boundary line.

Optionally, a boundary of each subsection is defined by a portion of a circumference of an image produced by a predetermined sized endoscope and a portion of a circumference of an image produced by a second predetermined sized endoscope, a vertical line through a center of the image, a horizontal line through the center of the image, and/or an image boundary line.

Optionally, a boundary of a subsection is defined by at least a portion of a circumference of an image produced by a first predetermined sized endoscope and a portion of a circumference of an image produced by a second predetermined sized endoscope, wherein a diameter of an image produced by the second predetermined sized endoscope is larger than the diameter of an image produced by the first predetermined sized endoscope.

Optionally, each of the at least two sections are segmented into four subsections.

Optionally, a boundary of each subsection is defined by a portion of a circumference of an image produced by a predetermined sized endoscope and a portion of a circumference of an image produced by a second predetermined sized endoscope, a vertical line through a center of the image, a horizontal line through the center of the image, and/or an image boundary line.

Optionally, the type of endoscope is a 4 mm endoscope, a 5 mm endoscope, or a 10 mm endoscope. In some embodiments, the type of endoscope comprises an alignment of the endoscope.

According to various aspects, a method comprises receiving image data representing an image from a video camera coupled to an endoscope; segmenting the image into at least two sections; segmenting each of the at least two sections into a plurality of subsections; calculating a representative pixel value for each of the subsections; determining what type of endoscope is coupled to the video camera based on the representative pixels values for each of the subsections; and adjusting a parameter of the video camera based on the type of endoscope.

According to various aspects, a non-transitory computer-readable storage medium storing instructions configured to be executed by a surgical system and to cause the surgical system to: configured to be executed by an endoscopic system and to cause the endoscopic system to: receive image data representing an image from a video camera coupled to an endoscope; segment the image into at least two sections; segment each of the at least two sections into a plurality of subsections; calculate a representative pixel value for each of the subsections; determine what type of endoscope is coupled to the video camera based on the representative pixels values for each of the subsections; and adjust a parameter of the video camera based on the type of endoscope.

It will be appreciated that any of the aspects, features and options described in view of the system apply equally to the method and computer-readable storage medium, and vice versa. It will also be clear that any one or more of the above aspects, features and options can be combined. According to an aspect, any one or more of the characteristics of any one or more of the systems, methods, and/or computer-readable storage mediums recited above may be combined, in whole or in part, with one another and/or with any other features or characteristics described elsewhere herein.

BRIEF DESCRIPTION OF THE FIGURES

Features will become apparent to those of ordinary skill in the art by describing in detail exemplary embodiments with reference to the attached drawings in which.

DETAILED DESCRIPTION

Reference will now be made in detail to implementations and embodiments of various aspects and variations of systems and methods described herein. Although several exemplary variations of the systems and methods are described herein, other variations of the systems and methods may include aspects of the systems and methods described herein combined in any suitable manner having combinations of all or some of the aspects described.

Disclosed are systems and methods for automatically identifying an endoscope that is coupled to an endoscopic video camera/light system and automatically adjusting a parameter of the video camera/light system based on the identified endoscope coupled to the endoscopic video camera/light system. These parameters can include selecting one or more settings of the display or processing of images thereby acquired.

Images from an endoscopic video camera are typically circular when displayed on a display system, due to the physical construction of the scope, depending on the magnification of the scope and/or the coupler which connects the scope to the camera. The available display area outside the circular image can sometimes be black and the diameter of the image relative to the total available display area (i.e., frame size or image boundary) can depend on the magnification of the scope, and/or the magnification of the coupler (if any), which in turn can depend on the particular optics within the scope and/or the coupler. For the purposes of this application, the term "black" regarding black pixels does not have to mean absolute black or the blackest value achievable by the equipment being used. Rather, it means that a specified minimum degree of blackness is present. Any reasonable threshold value can be used (e.g., for pixel color and/or intensity) to determine whether a particular pixel is black or not.

Figure 1:
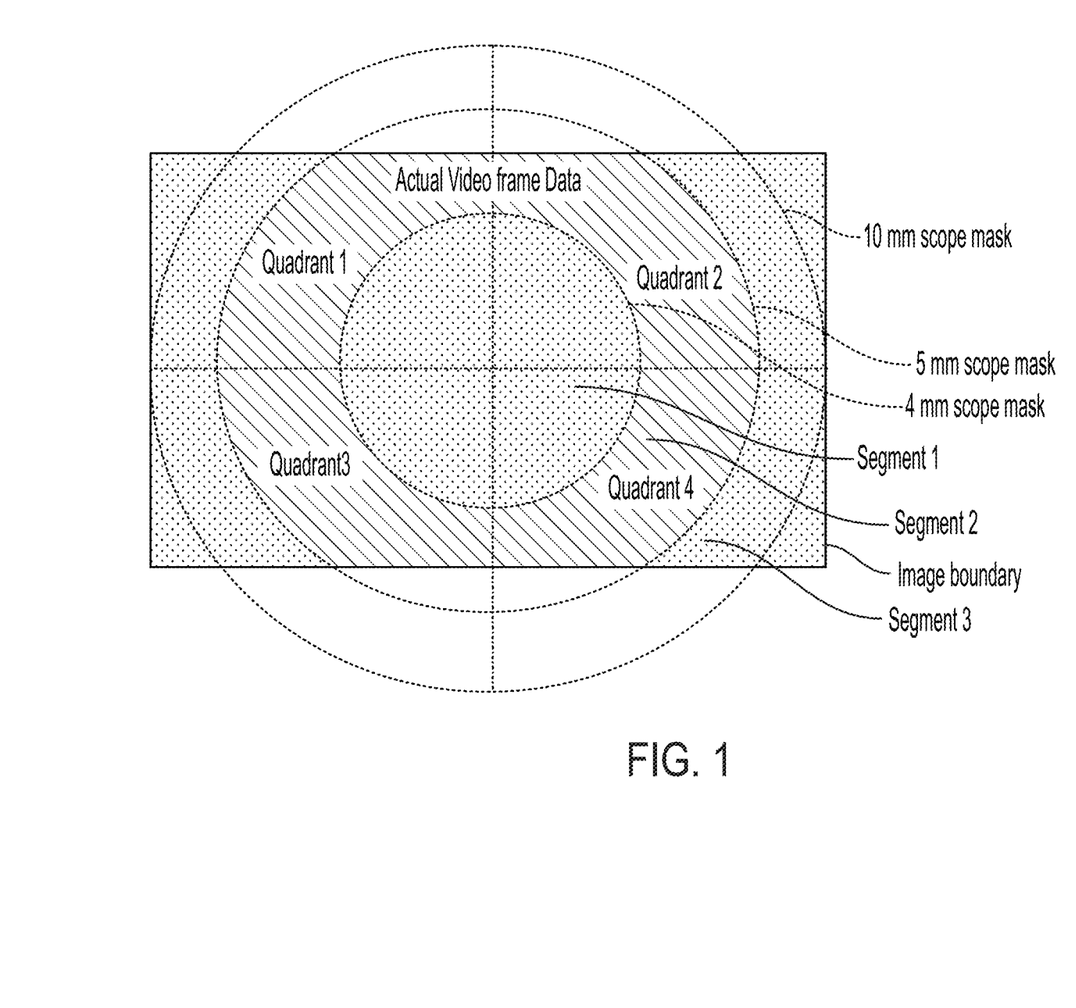
FIG. 1 illustrates exemplary video frames resulting from various endoscopes.

FIG. 1 shows an example of an image contained in a video frame generated by a video camera coupled to various endoscopes. As shown in FIG. 1, the diameter of an image produced by a 10 mm scope mask is larger than the diameter of an image produced by a 5 mm scope mask and a 4 mm scope mask. The mask can refer to the active area of the image from an endoscope. Although not shown, the diameter of these images can be surrounded by a black area in the unused (i.e., inactive) portion of the image boundary. For the bigger diameter scope mask, the black area surrounding the circular image in the unused portion of the frame would be smaller.

Thus, the actual image size (i.e., circular image) relative to the total image boundary (i.e., total frame size) can be an indication of the type of endoscope that is attached to the camera/light system. The image size, or conversely, the amount of unused (i.e., black) display area outside the image, can therefore be used to infer physical characteristics of the scope such as the size of the endoscope that is attached to the camera/light system. Thus, the image size (or the amount of black space) can be used as a basis to automatically detect the type of scope being used and/or select the settings for various image processing and display parameters which are most appropriate for that scope.

Figure 2:
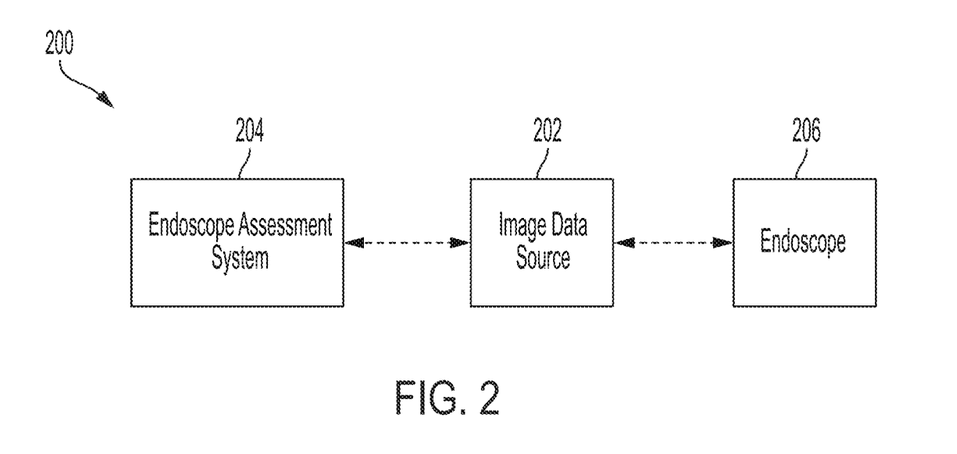
FIG. 2 depicts a system for assessing endoscope type, in accordance with some embodiments.

FIG. 2 depicts a system 200 for assessing endoscope type, in accordance with some embodiments.

As shown, system 200 may include image data source 202, endoscope assessment system 204, and endoscope 206. Each of these components may be communicatively coupled with one another such that they may send and receive electronic information via network communication amongst one another. As shown in the example of FIG. 2, assessment system 204 may be communicatively coupled to image data source 202. In some embodiments, assessment system 204 may be communicatively coupled to image data source 202 and to endoscope 206. In some embodiments, endoscope 206 can acquire and transmit image data from within the body to image data source 202. In some embodiments, endoscope 206 is coupled to image data source using a coupler. The coupler can allow for connection of the endoscope to the image data source, transmitting image data from the endoscope to the image data source, and/or focusing the image data on a sensor (e.g., camera head sensor) of the image data source.

In some embodiments, image data source 202 may be any electronic source for medical or surgical images and/or video, such as an image or video capture device, an image-capture and/or video-capture endoscope, an image or video broadcasting or relaying device, one or more servers, and/or one or more databases or repositories. Image data source 202 may be configured to transmit image data (e.g., medical/surgical image data and/or medical/surgical video data) to endoscope assessment system 204 by any wired or wireless electronic communication medium, including by any suitable network communication protocol. In some embodiments, the image data source can be an endoscopic camera/light source coupled to endoscope 206.

In some embodiments, endoscope assessment system 204 may be any device or system comprising one or more computer processors configured to receive image data, assess and/or process the received image data, and to generate and transmit one or more output signals in accordance with the results of the image assessment. In some embodiments, assessment system 204 may be provided, in whole or in part, as all or part of a desktop computing device, laptop, tablet, mobile electronic device, dedicated medical image processing device, computing module, processor, server, cloud computing system, distributed computing system, or the like. In some embodiments, endoscope assessment system 204 may be provided locally with respect to endoscope 206 (e.g., in the surgical suite), while in some embodiments endoscope assessment system 204 may be provided remotely from endoscope 206 (e.g., outside the surgical suite, elsewhere in a hospital, at a remote server location, etc.).

In some embodiments, assessment system 204 may be configured to receive image data (e.g., image and/or video data showing a surgical image) from image data source 202 and to process the image to determine the type of endoscope 206 coupled to image data source 202 based on the image data received. In some embodiments, assessment system 204 can process the image data to output the processed image to a display device such as a monitor. In some embodiments, assessment system 204 may be configured to determine the type of endoscope and adjust at least one parameter of the image data source in accordance with the techniques discussed below with reference to FIG. 3.

In some embodiments, assessment system 204 may be configured to send one or more instruction or control signals to image data source 202; in some embodiments, as discussed in detail herein, the instruction or control signal may be sent by assessment system 204 in accordance with the determined type of endoscope based on analysis of the image data received. For example, in some embodiments, assessment system 204 can optimize the image data source parameters (e.g., video gain levels, sharpness level, light source level, camera shutter speed, gamma level, etc.) based on the type of endoscope 206.

As discussed above, in some embodiments, image data source 202 may be configured to be modified in accordance with an instruction signal or control signal received from endoscope assessment system 204. In some embodiments, image data source 202 may be configured to receive instruction signals and/or control signals from endoscope assessment system 204 by any wired or wireless electronic communication medium, including by any suitable network communication protocol.

Figure 3:
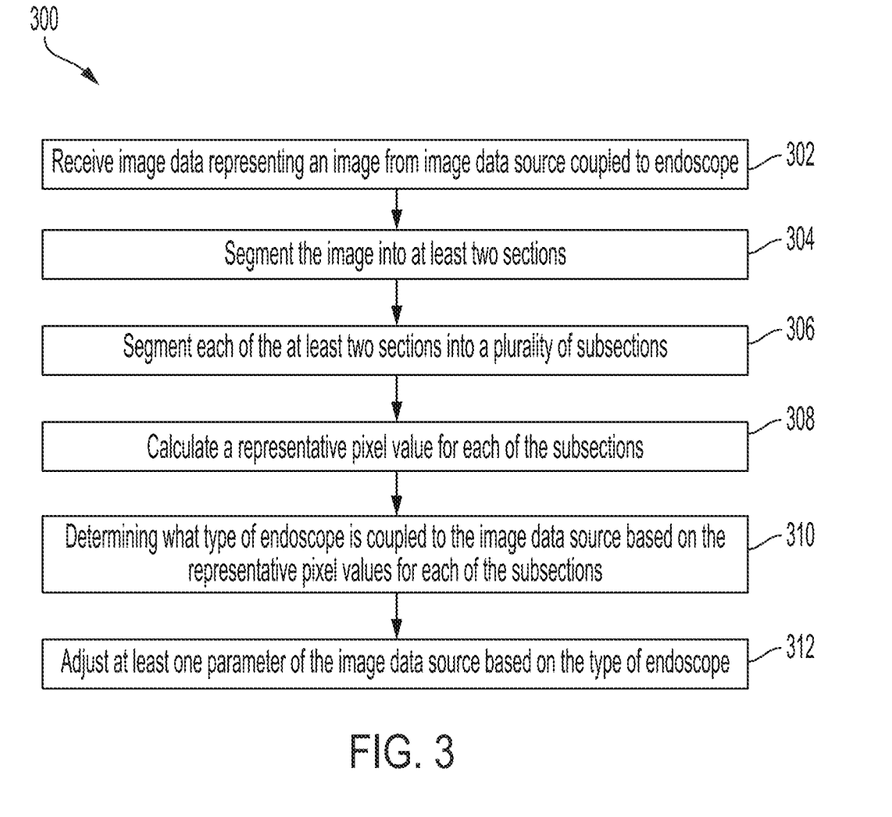
FIG. 3 depicts a flowchart representing an exemplary method 300 for determining the endoscope type, in accordance with some embodiments.

FIG. 3 depicts a flowchart representing an exemplary method 300 for determining the endoscope type, in accordance with some embodiments.

As described below in detail, method 300 may enable an endoscope assessment system to receive surgical images or videos, to process the surgical images or videos to determine the type of endoscope coupled to the image data source, and to automatically adjust at least one parameter of the image data source based on the type of endoscope coupled to the image data source.

In some embodiments, method 300 may be carried out, in whole or in part, by one or more of the components of a system for assessing endoscope type, such as system 200 described above with respect to FIG. 2. In some embodiments, any one or more of the aspects of method 300 may be combined, in whole or in part, with any one or more of the aspects of FIG. 2, and/or with any one or more of the systems, methods, devices, and/or techniques described elsewhere herein.

At block 302, in some embodiments, the system may receive image data representing an image. The image can be from an image data source and the image data source can be coupled to an endoscope. In some embodiments, the image may be of a surgical environment. In the example of system 200, endoscope assessment system 204 may receive image data representing an image from image data source 202.

The image data received by the system may be in the form of a still image or one or more frames of a video image, and may depict a surgical environment (e.g., an area in and/or near a tissue segment on which surgery is being performed) with an unknown endoscope coupled to the image data source. The image data may be received from an image or video capture device, an image or video broadcasting or relaying device, one or more servers, and/or one or more databases or repositories. The image data received may be received via any suitable form of electronic communication, including wired and/or wireless network communication.

The image data received by the system may comprise a plurality of pixels. One or more of the plurality of pixels constituting the image data may, in some embodiments, be associated with one or more values indicating a brightness (e.g., intensity) for the pixel. In some embodiments, a pixel may be associated with a plurality of values, with each value representing a different color-channel for the pixel. In some embodiments, each pixel may comprise three color-channel values, e.g., one value each for a red, green, and blue color-channel for each pixel. In some embodiments, one or more of the plurality of pixels constituting the image data may be associated with one or more values indicating a luminance for the pixel. Luminance of a pixel is the brightness of the pixel separated from its color (chroma) component. This can be calculated using color space conversion. For example, it can be RGB to YCbCr, where Y is the luminance value.

In some embodiments, the system may perform one or more image pre-processing techniques on the received image data (not shown in FIG. 3). For example, the system may perform cropping, alignment, and/or re-sizing (e.g., scaling) of the received image data before additional processing steps are performed.

In some embodiments, a cropping procedure may comprise identifying a region-of-interest (ROI) in the image data received, such that additional image processing techniques such as those described below may be performed only on the ROI selected, rather than on the entire original image. In some embodiments, an ROI may be selected manually by a user of the system. In some embodiments, an ROI may be selected automatically by one or more algorithms. In some embodiments, an ROI may be selected automatically as a predefined area (e.g., a predefined rectangular area of a given image size, e.g., a given pixel size) within a field of view of the received image data. In some embodiments, an ROI may be selected automatically as a region defined by a finding circle image processing approach, in which intersection points between a scope edge and a diagonal line of an image frame are used as reference points to calculate an inner rectangle defining the ROI.

In some embodiments, an alignment procedure may comprise rotating or aligning all or part of the received image data, such that additional image processing techniques such as those described below may be performed only on the aligned image, rather than on the entire original image.

In some embodiments, a scaling procedure may comprise scaling (e.g., resizing) all or part of the received image data, such that additional image processing techniques such as those described below may be performed only on the scaled image, rather than on the entire original image. For example, an image may be reduced in size such that the reduced-size, downscaled image may be used for one or more of the image processing techniques described below, rather than the original full-size image.

In some embodiments, more than one of the image pre-processing techniques may be performed on the same image data. For example, a single image frame may be subject to any two or more image preprocessing techniques before proceeding to the image processing techniques discussed below. In some embodiments, no image preprocessing techniques may be employed (e.g., the raw image data initially received may be used for the image processing steps described below).

At block 304, in some embodiments, the method may segment the received image into at least two sections. For example, each incoming image/video frame can be segmented into at least two sections. In some embodiments, the image can be segmented into at least three sections, into at least four sections, or into at least five sections. In some embodiments, at least one of the boundaries of a section can be the image boundary line(s) (i.e., frame size boundary). In some embodiments, at least one of the boundaries of a section can be a vertical line through the center of the image. In some embodiments, at least one of the boundaries of a section can be a horizontal line through the center of the image. In some embodiments, the boundaries of a section can be defined by the image boundary line(s), a vertical line through the center of the image, and/or a horizontal line through the center of the image.

Figure 4:
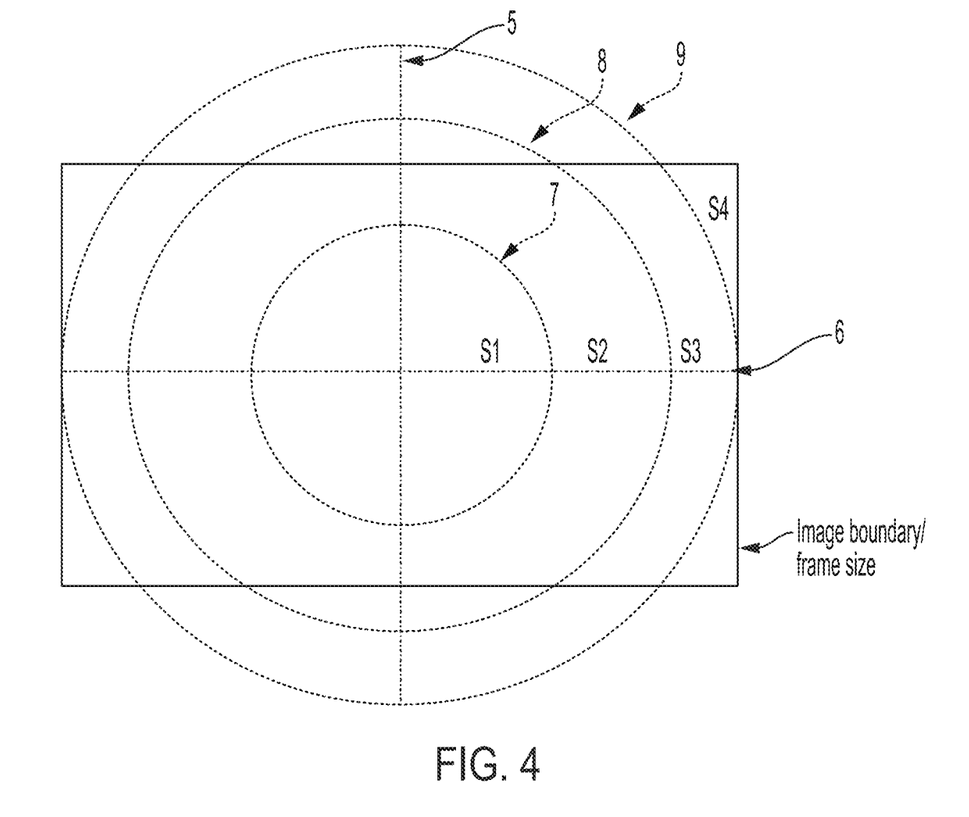
FIG. 4 illustrates exemplary sections and subsections resulting from segmenting the image received form an image data source coupled to an endoscope, in accordance with some embodiments.

In some embodiments, the at least two sections can be defined by a vertical line through the center of the image shown by line 5 in FIG. 4, thereby segmenting the image into two sections, one on each side of vertical line 5 that are bounded by the image boundary lines and vertical line 5. In some embodiments, the at least two sections can be defined by a horizontal line through the center of the image shown by line 6 in FIG. 4, thereby segmenting the image into two sections, one on each side of horizontal line 6 that are bounded by the image boundary lines and horizontal line 6. In some embodiments, the at least two sections can be defined by a vertical and a horizontal line through the center of the image, thereby segmenting the image into four quadrants as shown in FIG. 4 as Quadrant 1, Quadrant 2, Quadrant 3, and Quadrant 4 that are bounded by the image boundary lines, vertical line 5, and horizontal line 6. The image can also be segmented in a variety of other ways besides those described above.

At block 306, in some embodiments, the system may segment each of the at least two sections into a plurality of subsections. For example, each individual section of the image/video frame can further be segmented into a plurality of subsections. In some embodiments, the segmented sections can be further segmented into at least two subsections, into at least three subsections, into at least four subsections, or into at least five subsections. In some embodiments, at least one boundary of a subsection can be the portion of the circumference of an image produced by a predetermined sized endoscope within the individual section. The at least one boundary of the subsection can be identified manually through experiments to calculate the non-active area of the scope mask for a given scope. In some embodiments, at least one boundary of a subsection can be the portion of the circumference of an image produced by a different predetermined sized endoscope within the individual section. In some embodiments, the diameter of an image produced by a second predetermined sized endoscope is greater than the diameter of an image produced by a first predetermined sized endoscope. In some embodiments, the diameter of an image produced by a third predetermined sized endoscope is larger than the diameter of an image produced by a first and/or second predetermined sized endoscope. In some embodiments, the portion of the circumference of an image produced by a predetermined sized endoscope within the section can be an arcuate boundary. In some embodiments, at least one of the boundaries of a subsection can be the image boundary line(s) (i.e., frame size boundary line(s)). In some embodiments, at least one of the boundaries of a subsection can be a vertical line through the center of the image. In some embodiments, at least one of the boundaries of a subsection can be a horizontal line through the center of the image. In some embodiments, the boundaries of a subsection can be defined by the image boundary line(s), a vertical line through the center of the image, a horizontal line through the center of the image, the portion of the circumference of an image produced by a first predetermined sized endoscope within the section, and/or the portion of the circumference of an image produced by a second predetermined sized endoscope within the section. In some embodiments, the boundaries of a subsection can be defined by a portion of the circumference of an image produced by a first predetermined sized endoscope within the section and the image boundary line(s), a vertical line through the center of the image, a horizontal line through the center of the image, and/or the portion of the circumference of an image produced by a second predetermined sized endoscope within the section.

For example, subsection S1 of Quadrant 1 illustrated in FIG. 4 is bounded by vertical line 5, horizontal line 6, and the portion of the circumference of an image produced by a first predetermined sized endoscope mask 7 (e.g., 4 mm endoscope mask). Subsection S2 of Quadrant 1 illustrated in FIG. 4 is bounded by vertical line 5, horizontal line 6, image boundary line, portion of the circumference of an image produced by a first predetermined sized endoscope mask 7, and portion of the circumference of an image produced by a second predetermined sized endoscope mask 8 (e.g., 5 mm endoscope mask). Subsection S3 of Quadrant 1 illustrated in FIG. 4 is bounded by horizontal line 6, image boundary line, portion of the circumference of an image produced by a second predetermined sized endoscope mask 8, and portion of the circumference of an image produced by a third predetermined sized endoscope mask 9 (e.g., 10 mm endoscope mask). Subsection S4 of Quadrant 1 illustrated in FIG. 4 is bounded by image boundary lines and a third predetermined sized endoscope mask 9. This analysis of subsection S1-S4 can also be applied with the other three quadrants. In some embodiments, the plurality of subsections are sequentially positioned outwardly from a center of the image toward an outer corner of the image.

Segmentation of the image into multiple sections and subsections can help analyze the image for various purposes such as shutter control, object detection, color processing, and other events. Segmentation of the image into multiple sections and subsections can improve accuracy of the scope detection. For example, for a 10 mm scope detection, when calculating the number of black pixels vs gray pixels only, similar values occur between a 10 mm centered and a 4 mm off-centered scope and can result in a false detection. Segmentation can assess that the 5 mm scope is off-centered and prevent a false detection. Similarly, for a shutter control example, if there is a large cavity that the camera is looking at, there can be instances where the foreground portion can get oversaturated with respect to the background. With segmentation, each of these localized segments can be monitored to detect that and set the shutter speed appropriately.

In some embodiments, the image data can be converted into an appropriate color space for further analysis. Color space conversion can be used to calculate luminance and chroma parameters. For example, in some embodiments, the image data may include RGB data and can be converted to YCbCr data. In some embodiments, the conversion of the image data into the appropriate color space can occur before, after, or simultaneously with the segmentation of the image (i.e., Steps 304 and 306).

At block 308, in some embodiments, the method can calculate a representative pixel value for each of the subsections. In some embodiments, the representative pixel value is a luminance value. In some embodiments, the luminance value includes a representative luminance value for the plurality of pixels within each subsection. In some embodiments, the representative luminance value for a given amount of pixels within an image boundary can be calculated by the sum of luminance of all pixels in a given segment divided by the number of pixels in a given segment. For example, the representative luminance value can be calculated by the following equation: $\Sigma_{i=1}{}^n L/n$, where "L" is the luminance value for each pixel "i", and "n" is the number of pixels. In some embodiments, the representative luminance value for a given amount of pixels within an image boundary can be calculated by determining the maximum and minimum luminance value of the pixels within the image boundary and averaging them. For example, the representative luminance value can be calculated by the following equation: (MAX-L+MIN-L)/2, where MAX-L and MIN-L are the maximum and minimum values of the pixels within the given image boundary.

In some embodiments, the luminance value includes the standard deviation of luminance for the plurality of pixels within each subsection. The standard deviation for a given amount of pixels within an image boundary can be calculated by subtracting each pixel value in a segment from the average and calculating the mean of those values. In some embodiments, the luminance value includes both the representative luminance and the standard deviation of luminance for the plurality of pixels within each subsection. In some embodiments, a histogram of the image can validate the distribution of luminance. A histogram of an image can be the measure of entropy, i.e., for an 8-bit color or 24 bit RGB representation. A pixel can have values/levels between 0-256. A histogram can show how many pixels are present in an image at each pixel value/level. To simplify validation, an assumption can be made that levels between 0-64 are shadows, 64-196 are midtones, and 196-256 are highlights. Considering all these, when a histogram is sampled in the process disclosed herein, the histogram can show if there is enough distinction present between the active area and the rest of the image for an accurate detection. For example, if the percentage of shadows is 90%, the image can be underexposed and scope detection should not be performed in this condition.

At block 310, the method can determine what type of endoscope is coupled to the image data source based on the representative pixel values for each of the subsections. In some embodiments, this determination can include comparing the representative luminance for each subsection with threshold luminance values for each subsection for a plurality of endoscope types. For example, for every incoming frame, the representative luminance for each subsection can be calculated. These values can be stored in a memory and/or compared to a table of threshold luminance values. In some embodiments, the threshold luminance values can be determined through experiments to characterize each scope type (e.g., manually). In some embodiments, if the representative luminance value for each subsection falls within the threshold luminance range for each subsection for a given endoscope type of the plurality of endoscope types, the type of endoscope coupled to the image data source is the given endoscope type. Each of the plurality of endoscope types can have a different threshold luminance range for each subsection.

For example, the following Table 1 and Table 2 provide example threshold luminance ranges for each subsection for a center and right aligned 10 mm scope type, respectively.

TABLE 1

| | Quadrant 1 | Quadrant 2 | Quadrant 3 | Quadrant 4 | Scope Type |
|---|---|---|---|---|---|
| Segment 1 | >2^4 | >2^4 | >2^4 | >2^4 | 10 MM |
| Segment 2 | >2^4 | >2^4 | >2^4 | >2^4 | Centered |
| Segment 3 | <2^4 | <2^4 | <2^4 | <2^4 | |
| Segment 4 | <2^4 | <2^4 | <2^4 | <2^4 | |

TABLE 2

| | Quadrant 1 | Quadrant 2 | Quadrant 3 | Quadrant 4 | Scope Type |
|---|---|---|---|---|---|
| Segment 1 | >2^4 | >2^4 | >2^4 | >2^4 | 10 MM |
| Segment 2 | <2^4 | >2^4 | <2^4 | >2^4 | Right |
| Segment 3 | <2^4 | >2^4 | <2^4 | >2^4 | Aligned |
| Segment 4 | <2^4 | <2^4 | <2^4 | <2^4 | |

For a 8-bit color image, which is a 24-bit RGB image, the luminance can have values/levels between 0-256 (i.e., 2 to the power of 8 or 2^8=256). In the Tables, any segment representative values less than 2^4=32 can be considered below threshold and the rest above. In the scope mask diagram, depending on the values calculated from each segment, a classification can be performed. Similar, Tables can exist for a 4 mm endoscope, 5 mm endoscope, etc.

In some embodiments, the various threshold luminance ranges for each subsection for a given type of endoscope may have been previously set up to contain the possible scope types and threshold luminance values and/or appropriate parameters for the processing or display of images, for multiple possible endoscopes types. The various threshold luminance ranges for each subsection for a given type of endoscope may have been determined experimentally to being stored in the endoscope assessment system.

Thus, the type of scope can be automatically detected, and the preferred parameter settings(s) for the endoscope can be automatically identified and selected.

In some embodiments, the type of endoscope can be a 4 mm endoscope, a 5 mm endoscope, or a 10 mm endoscope. In some embodiments, the type of endoscope can also include whether the scope is right aligned, left aligned, top aligned, or bottom aligned. Alignment can be referred to misalignment of the scope from the center of the image. This can occur from improper alignment between the scope and the coupler. For example, in Table 2 above, the difference from Table 1 is segment 3's quadrants 2 and 4 have representative luminance values greater than 23 (2^4) and segment 2's quadrants 1 and 3 have representative values less than 32. As such, an identification of the scope can be determined even if the scope is aligned off-center.

In some embodiments, the image data can be a single frame of a video image. As such, steps 302-310 can be conducted using the single frame of a video image. In some embodiments, the steps 302-310 can be repeated over a plurality of frames of a video image. This can help ensure that there are no false detections of the type of endoscope coupled to the image data source.

At block 312, the method can automatically adjust at least one parameter of the image data source based on the type of endoscope. In some embodiments, the parameters can be at least one of video gain level, sharpness level, camera shutter speed, or gamma level. In some embodiments, the image data source (e.g., a video camera) includes a light source. As such, the at least one parameter can include a light source setting. For example, between a 10 mm scope and a 5 mm scope, the laser IR light output for fluorescence imaging can be different to maintain the image quality. Different types of endoscopes may require a different light source setting. For example, of a 4 mm, 5 mm, and 10 mm laparoscope, the 5 mm laparoscope may need the highest amount of light, followed by the 4 mm and 10 mm laparoscope. A 4 mm Arthroscope scope is normally looking at a much smaller cavity and the target is much closer around 8 mm. A Laparoscope is normally looking at a much larger cavity and the typical working distance is 50 mm. As such, a 5 mm Laparoscope may need more white light than a 4 mm Arthroscope. This is just one example, but it is scope specific and not simply based on the actual diameter of the scope. For instance, working distance of the scope can be key. In some embodiments, the method can adjust at least one parameter for processing or displaying the images acquired by the image data source.

In indocyanine green applications ("ICG"), ICG can be used as a marker in the assessment of the perfusion of tissues and organs in many areas of medicine. The light needed for the excitation of the fluorescence can be generated by a near infrared light source which can be coupled to the endoscope (i.e., image data source). The endoscopy camera can allow the absorption of the ICG fluorescence to be recorded in real time, which means that the perfusion can be assessed and documented. A 5 mm or a 10 mm endoscope could be used with this ICG perfusion procedure. However, a 10 mm endoscope can be almost four times brighter than a 5 mm endoscope. As such, the infrared light source may need to provide a higher power for the 5 mm endoscope when compared to the 10 mm endoscope. In addition, the video signal gain when using a 5 mm endoscope may need to be higher than the 10 mm endoscope.

In some embodiments, the steps 302-312 can be repeated over a plurality of frames of a video image. This can help ensure that there are no false detections of the type of endoscope coupled to the image data source. In addition, this can help detect if the type of endoscope has changed. Thus, the system can perform method 300 periodically or continuously to detect if there is any change in the type of endoscope coupled to the image data source.

In some embodiments, a user can perform white balancing prior to starting the use of the image data source. White balancing can be a process to normalize the RGB values (i.e., primary colors) to get white of a given white point or color temperature. The endoscope coupled to the image data source can be looking at a white target for white balancing. In some embodiments, white balancing of the image data source can trigger the start of method 300.

Figure 5:
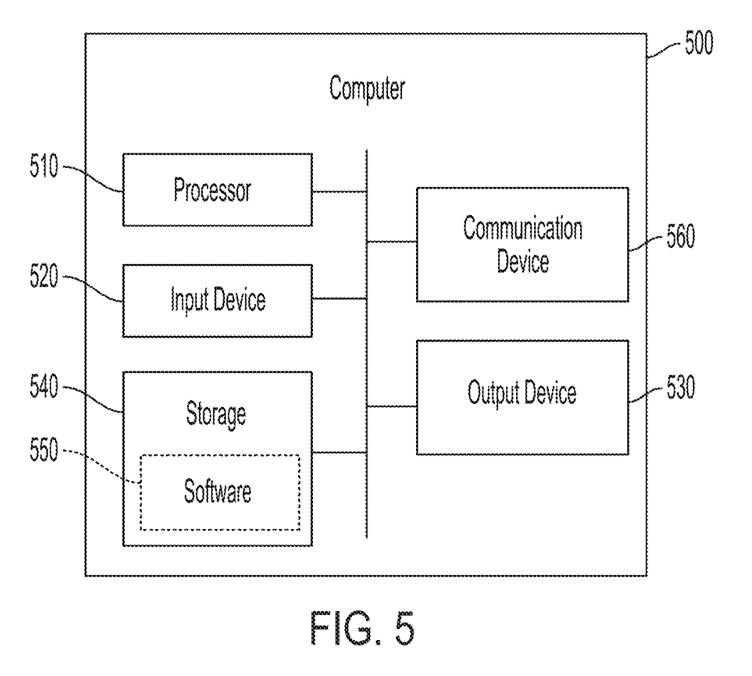
FIG. 5 depicts a computer, in accordance with some embodiments.

FIG. 5 illustrates a computer, in accordance with some embodiments. Computer 500 can be a component of a system for assessing endoscope type, such as system 200 and/or any of its subcomponents described above with respect to FIG. 2. In some embodiments, computer 500 may be configured to execute a method for assessing endoscope type, such as all or part of method 300 described above with respect to FIG. 3.

Computer 500 can be a host computer connected to a network. Computer 500 can be a client computer or a server. As shown in FIG. 5, computer 500 can be any suitable type of microprocessor-based device, such as a personal computer; workstation; server; or handheld computing device, such as a phone or tablet. The computer can include, for example, one or more of processor 510, input device 520, output device 530, storage 540, and communication device 560.

Input device 520 can be any suitable device that provides input, such as a touch screen or monitor, keyboard, mouse, or voice-recognition device. Output device 530 can be any suitable device that provides output, such as a touch screen, monitor, printer, disk drive, or speaker.

Storage 540 can be any suitable device that provides storage, such as an electrical, magnetic, or optical memory, including a RAM, cache, hard drive, CD-ROM drive, tape drive, or removable storage disk. Communication device 560 can include any suitable device capable of transmitting and receiving signals over a network, such as a network interface chip or card. The components of the computer can be connected in any suitable manner, such as via a physical bus or wirelessly. Storage 540 can be a non-transitory computer-readable storage medium comprising one or more programs, which, when executed by one or more processors, such as processor 510, cause the one or more processors to execute methods described herein, such as all or part of method 300 described above with respect to FIG. 3.

Software 550, which can be stored in storage 540 and executed by processor 510, can include, for example, the programming that embodies the functionality of the present disclosure (e.g., as embodied in the systems, computers, servers, and/or devices as described above). In some embodiments, software 550 can be implemented and executed on a combination of servers such as application servers and database servers.

Software 550 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 540, that can contain or store programming for use by or in connection with an instruction execution system, apparatus, or device.

Software 550 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 500 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 500 can implement any operating system suitable for operating on the network including a machine learning operating system. Software 550 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. Finally, the entire disclosure of the patents and publications referred to in this application are hereby incorporated herein by reference.

The invention claimed is:

1. An endoscopic system comprising:
one or more processors configured to:
receive image data representing an image from a video camera coupled to an endoscope;
segment the image into at least two sections;
segment each of the at least two sections into a plurality of subsections;
calculate a representative pixel value for each of the subsections, wherein calculating the representative pixel value for each of the subsections comprises calculating a single representative luminance for a plurality of pixels within each subsection;
determine what type of endoscope is coupled to the video camera based on the representative pixels values for each of the subsections; and
adjust a parameter of the video camera based on the type of endoscope, wherein the parameter comprises at least one of video gain level, sharpness level, camera shutter speed, or gamma level.

2. The endoscopic system of claim 1, wherein the parameter comprises light source setting.

3. The endoscopic system of claim 1, wherein the parameter is a parameter for processing or displaying images acquired by the video camera.

4. The endoscopic system of claim 1, wherein the type of endoscope determined is dependent upon a physical characteristic of the endoscope.

5. The endoscopic system of claim 4, wherein the physical characteristic of the endoscope comprises a size of a scope mask of the endoscope.

6. The endoscopic system of claim 1, wherein determining what type of endoscope is coupled to the video camera comprises comparing the representative luminance for each subsection with threshold luminance values for each subsection for a given endoscope type.

7. The endoscopic system of claim 1, wherein a boundary of each section is defined by a vertical line through a center of the image, a horizontal line through the center of the image, and/or an image boundary line.

8. The endoscopic system of claim 7, wherein a boundary of each section is defined by a vertical line through a center of the image, a horizontal line through the center of the image, and an image boundary line.

9. The endoscopic system of claim 1, wherein the image is segmented into four sections.

10. The endoscopic system of claim 1, wherein a boundary of each subsection is defined by a portion of a circumference of an image produced by a predetermined sized endoscope and a portion of a circumference of an image produced by a second predetermined sized endoscope, a vertical line through a center of the image, a horizontal line through the center of the image, and/or an image boundary line.

11. The endoscopic system of claim 1, wherein a boundary of a subsection is defined by at least a portion of a circumference of an image produced by a first predetermined sized endoscope and a portion of a circumference of an image produced by a second predetermined sized endoscope, wherein a diameter of an image produced by the second predetermined sized endoscope is larger than the diameter of an image produced by the first predetermined sized endoscope.

12. The endoscopic system of claim 1, wherein each of the at least two sections are segmented into four subsections.

13. The endoscopic system of claim 12, wherein a boundary of each subsection is defined by a portion of a circumference of an image produced by a predetermined sized endoscope and a portion of a circumference of an image produced by a second predetermined sized endoscope, a vertical line through a center of the image, a horizontal line through the center of the image, and/or an image boundary line.

14. The endoscopic system of claim 1, wherein the type of endoscope is a 4 mm endoscope, a 5 mm endoscope, or a 10 mm endoscope.

15. The endoscopic system of claim 14, wherein the type of endoscope comprises whether the endoscope is right aligned, left aligned, top aligned, and/or bottom aligned.

16. A method comprising:
- receiving image data representing an image from a video camera coupled to an endoscope;
- segmenting the image into at least two sections;
- segmenting each of the at least two sections into a plurality of subsections;
- calculating a representative pixel value for each of the subsections, wherein calculating the representative pixel value for each of the subsections comprises calculating a single representative luminance for a plurality of pixels within each subsection;
- determining what type of endoscope is coupled to the video camera based on the representative pixel values for each of the subsections; and
- adjusting a parameter of the video camera based on the type of endoscope, wherein the parameter comprises at least one of video gain level, sharpness level, camera shutter speed, or gamma level.

17. A non-transitory computer-readable storage medium storing instructions configured to be executed by a surgical system and to cause the surgical system to:
- configured to be executed by an endoscopic system and to cause the endoscopic system to:
  - receive image data representing an image from a video camera coupled to an endoscope;
  - segment the image into at least two sections;
  - segment each of the at least two sections into a plurality of subsections;
  - calculate a representative pixel value for each of the subsections, wherein calculating the representative pixel value for each of the subsections comprises calculating a single representative luminance for a plurality of pixels within each subsection;
  - determine what type of endoscope is coupled to the video camera based on the representative pixel values for each of the subsections; and
  - adjust a parameter of the video camera based on the type of endoscope, wherein the parameter comprises at least one of video gain level, sharpness level, camera shutter speed, or gamma level.

* * * * *